US005494893A

United States Patent [19]

Pettit et al.

[11] Patent Number: 5,494,893

[45] Date of Patent: Feb. 27, 1996

[54] STYLOSTATIN 2

[75] Inventors: George R. Pettit, Paradise Valley; Jayaram K. Srirangam, Tempe, both of Ariz.

[73] Assignee: Arizona Board of Regents, a body corporate acting on behalf of Arizona State University, Tempe, Ariz.

[21] Appl. No.: 338,384

[22] Filed: Nov. 14, 1994

[51] Int. Cl.[6] ........ C07K 5/12

[52] U.S. Cl. ........ 514/11; 530/317; 514/9

[58] Field of Search ........ 530/317; 514/11, 514/9

[56] References Cited

PUBLICATIONS

J. Org. Chem. 1992(57), 7217–7220, Pettit et al.

*Primary Examiner*—Howard E. Schain

*Attorney, Agent, or Firm*—Richard R. Mybeck

[57] ABSTRACT

The cytostatic cycloheptapeptide stylostatin 2 was isolated respectively, from the South and Western Pacific Ocean sponges Stylotella sp. and Phakellia costata. Structural determination was accomplished by utilizing high-field (500 MHz) 2D-NMR experiments and confirmed by an X-ray crystal structure determination to provide the assignment cyclo(Pro-Leu-Ile-Phe-Ser-Pro-Ile). The absolute configuration was established by chiral gas chromatographic analytical technique. The cyclic heptapeptide backbone was found to include a β-turn, type VIa, incorporating a cis peptide bond, at -Ser-Pro.

2 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 7 amino acids residues
( B ) TYPE: amino acid
( D ) TOPOLOGY: cyclic ( i i ) MOLECULE TYPE:
( A ) DESCRIPTION: cycloheptapeptide stylostatin 2

-continued ( i i i ) HYPOTHETICAL: no ( i v ) ANTI-SENSE: no ( v ) FRAGMENT TYPE: internal ( v i ) ORIGINAL SOURCE:
( A ) ORGANISM:
Stylotella sp. and Phakellia castada sponges
( D ) DEVELOPMENTAL STAGE: whole organism ( i x ) FEATURE:
( A ) NAME/KEY: stylostatin 2
( C ) IDENTIFICATION METHOD: by experiment using amino acid analysis, high resolution nuclear magnetic resonance, mass spectral analysis, single crystal X-ray structure determination and chiral gas chromatography
( D ) OTHER INFORMATION: stylostatin 2 is a cell growth inhibitory peptide with activity in murine lymphocytic leukemia (PS) cell line and human cancer cell growth inhibition (OVCAR 3 GI50 3.7 microgram/ml)

( x ) PUBLICATION INFORMATION:
( A ) AUTHORS:
PETTIT, GEORGE R.
SRIRANGAM, JAYARAM K.
HERALD, DELBERT L.
XU, JUN- PING
BOYD, MICHAEL R.
CICHACZ, ZIBIGNIEW A.
KAMANO, YOSHIAKI
SCHMIDT, JEAN M.
ERICKSON, KAREN L.
( B ) TITLE: Isolation, Structure and Conformational Analysis of Stylostatin 2: A New Marine Porifera Cycloheptapeptide
( C ) JOURNAL: Journal of Organic Chemistry
( D ) VOLUME:
( F ) PAGES:
( G ) DATE:
( H ) DOCUMENT NUMBER:
( I ) FILING DATE:

( x i ) SEQUENCE DESCRIPTION: SEQ ID NO: 1:

Pro Leu Ile Phe Ser Pro Ile
1 5

STYLOSTATIN 2

In part, this research was funded by Outstanding Investigator Grant CA44344-01-06 awarded by the National Cancer Institute, DHHS. The United States government may have certain rights to this invention.

INTRODUCTION

This invention relates generally to the field of agents which may be useful in the field of chemotherapy. More particularly, this invention relates to the discovery and structural elucidation of a new cycloheptapeptide, which has been shown to be cytostatic in vitro, designated herein as stylostatin 2.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions in their evolutionary chemistry to reach their present level of cellular organization, regulation and defense.

Marine sponges, however, have changed minimally in their physical appearance over the last 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. sea hare extracts were being used in Greece for their curative effect. This consideration along with the observation that marine animals, e.g., invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and antineoplastic and/or cytotoxic agents and might also lead to compounds which would be effective in the control and/or eradication of viral diseases. Further, these marine organisms were believed to possess potentially useful drug candidates of unprecedented structure which had eluded discovery by other methods of medicinal chemistry. Fortunately, these expectations have been realized, e.g., the discovery of the bryostatins, dolastatins and cephalostatins, many of which are now in preclinical or human clinical studies.

Those researchers presently involved in medicinal chemistry know well the time lag between the isolation of a new compound and its introduction to the market. This procedure takes several years and often takes decades. Accordingly, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop this necessary data approaches ten million dollars per compound. Such a large investment will be made only when there is a reasonable opportunity for it to be recovered. Absent such opportunity, there will be no investment and the research involving the discovery of these potentially life saving compounds will cease.

Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, Oct. 1989, for an overview of the testing protocol; Monks et al., "Feasibility of a High-Flux Anticancer Drug Screen Using a Diverse Panel of Cultured Human Tumor Cell Lines", 83 *J. Nat. Cancer Inst.*, No. 11, 757 (1991) and Paull, K. D., "Display and Analysis of Patterns of Differential Activity of Drugs Against Human Tumor Cell Lines; Development of Mean Graph and COMPARE Algorithm", 81 *J. Nat. Cancer Inst. Rpts.*, No. 14, 1088, (1989) for a description of the methods of statistical analysis. Each of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs materially from the compounds which are extracts of marine creatures possessing antineoplastic qualities. The collection and processing of these latter compounds from their natural sources ranges from the grossly impractical to the utterly impossible. Ignoring the ecological impact of such harvesting, the population of these creatures and the cost of collection and extraction make the process unworkable. Artificial synthesis of the active compounds is the only possible solution.

Therefore, the elucidation of the structure of these antineoplastic compounds is essential. After the structure has been determined, a means of synthesis must be determined. This is often a long and arduous procedure because of the idiosyncratic complexity of these naturally occurring, evolutionary modified compounds. In addition, research is necessary to determine whether any portion of the naturally occurring compound is irrelevant to the desired properties, so that focus can be had on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that inhibited cell growth relieves these conditions, thereby allowing the human thus affected to have a longer, more productive life. Little could be more utilitarian than this result.

The recognition of antineoplastic and tumor inhibiting activity as demonstrated by accepted NCI criteria as "utility" can promote research efforts in the United States and is unequivocally essential if those efforts are to obtain even a modest modicum of success.

The sole right obtained from the grant of a Letters Patent is to prevent others from exploiting the subject matter of the patent. This results in the protection of the inventor for a period adequate to allow the recoupment of investment. This in turn provides incentive and the means for further research.

BRIEF SUMMARY OF THE INVENTION

To date, many promising compounds have been developed from marine animals in general, and in particular Marine Porifera indigenous to tropical areas. This invention discloses a trace constituent extracted from sponges recollected in the Bismarck Archipelago of Papua, New Guinea. Stylostatin 2 was separated from a P388 (N.C.I. designation) active hexane-methanol-toluene fraction remaining from the chromatography of stylostatin 1, which was reported in the *Journal of Organic Chemistry*, 1992, pp. 7217–7220. A copy of this scheme, amended to include the extraction of stylostatin 2 appears herein. Stylostatin 1 and stylostatin 2 are structurally distinct.

Stylostatin 2 has been tested against the NCI 60 cell line panel, in quadruplicate, and yielded an average $GI_{50}$ of $6.2\times10^{-6}$ M, and a value for OVCAR 3 of 3.7 μg/ml. Similarly the $ED_{50}$ P388 is 0.022 μg/ml.

Accordingly, the primary object of the subject invention is the disclosure of a new in vitro cytostatic cycloheptapeptide designated herein as stylostatin 2 which is shown as follows:

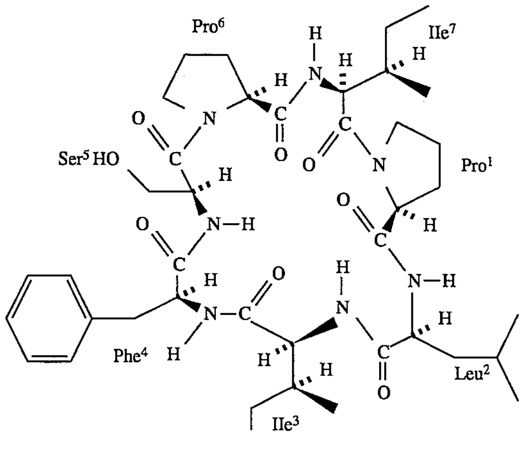

Still another object of the present invention is the structural elucidation of stylostatin 2.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

Statistical Definitions

The following measures are used to express drug activity by giving the drug dose which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

TGI, (Total Growth Inhibition), is the drug dose needed to yield zero percent growth, i.e., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to −50%, i.e., removes half of the cells originally present at the beginning of the experiment.

Each drug is tested at five (5) doses: 100—10—1—0.1—0.01 μg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

Percent Growth

At the start of an experiment, cells from the in vitro cell cultures are inoculated into the appropriate tubes or microtiter plates. One set of control tubes/plates is immediately counted to determine the number of cells at the start of the experiment. This is the "baseline count", or "$T_{zero}$ reading". At the end of the experiment (48 hours later), a second set of control tubes/plates is analyzed to determine the "Control Growth" value. The growth (or death) of cells relative to the initial quantity of cells is used to define the "Percent of Growth".

| | EXAMPLE:<br>Baseline Count = 20<br>Control Count = 200<br>(10-Fold Growth) |
|---|---|
| 100% Growth = Control Growth | 100% Growth = 200 |
| 50% Growth =<br>$T_{zero}$ + Control $-\frac{T}{2}$ zero | 50% Growth = 110 |
| 0% Growth = $T_{zero}$ | 0% Growth = 20 |
| −50% Growth = $T_{zero}/2$ | −50% Growth = 10 |

Separation of Stylostatin 2

The isolation scheme for stylostatin 1 was disclosed in *The Journal of Organic Chemistry*, 1992, Vol. 52, pp. 7217–7220. A systematic investigation for hitherto unknown trace compounds has led to the discovery of a new cycloheptapeptide designated herein as stylostatin 2.

Stylostatin 2 was first discovered in the Stylotella aurantium sponge, and was subsequently discovered in the sponge Phakellia costata. The separation scheme for isolating stylostatin 2 from Stylotella aurantium appears below:

Sheme I

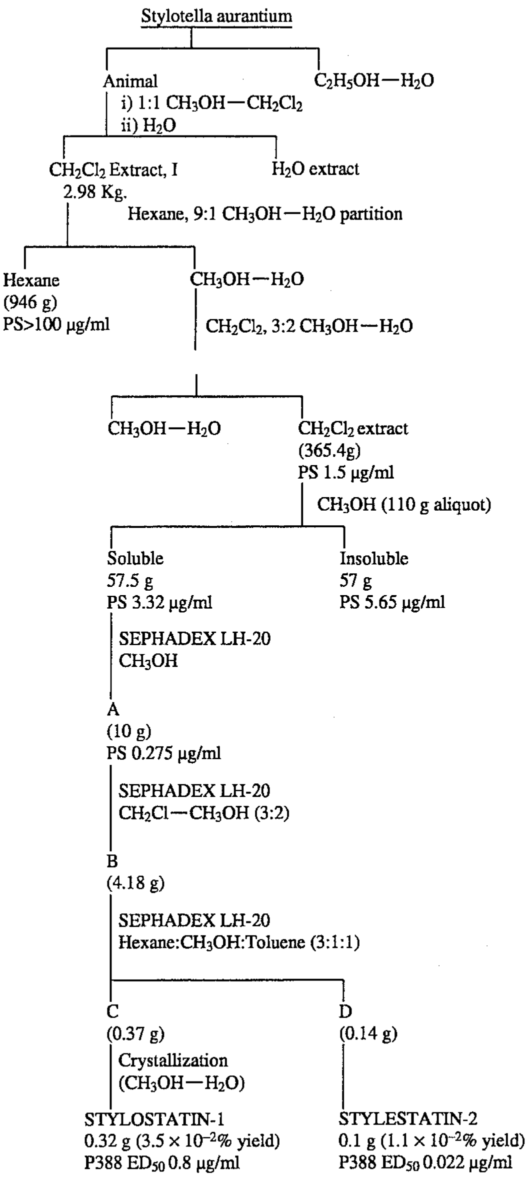

Marine Porifera indigenous especially to tropical ocean areas are rapidly increasing in importance as sources of potentially important new drugs. Illustrative of such promising constituents are the spongistatin and halichondrin/halistatin series of spirochetal/perhydropyrans with remarkable activity against a variety of murine and human cancer experimental systems. Presently, evidence is increasing that certain marine sponges also contain amino acid derivatives, usually as trace constituents, with significant cancer cell growth inhibitory properties such as the new cyclic peptides we discovered in Western Pacific and Indian Ocean Porifera. Other noteworthy examples include new biochemical probes of the discodermin (inhibits tumor promotion) and calyculin (tumor promoting) classes and the antithrombin cyclotheonamides.

In 1983 a Stylotella Sp. of marine sponge was collected in the Bismarck Archipelago of Papua New Guinea ("PNG"). A 1986 recollection (500 kg wet wt) was employed to isolate and characterize the cycloheptapeptide stylostatin 1 [cyclo (Pro-Phe-Asn-Ser-Leu-Ala-Ile)] which is a murine P388 lymphocytic leukemia (PS system) cell line inhibitor. Meanwhile Scheuer and colleagues have nicely determined the structure of the proline derived PS cell growth inhibitory and immunosuppressive antibiotic Palou'amine from the Western Pacific Stylotella agminata. Continuation of a detailed investigation of the PNG Stylotella sp. for new antineoplastic constituents has led to a new human cancer cell growth inhibitory (e.g. OVCAR 3—$GI_{50}$ 3.7 μg/ml) cycloheptapeptide designated stylostatin 2.

A 0.14 g PS active hexane-methanol-toluene (3:1:1) fraction from a SEPHADEX LH-20 column chromatogram obtained during isolation of stylostatin 1 was finally separated by fractional crystallization from aqueous methanol. The principal product ($2\times10^{-5}$ % yield) was the new cancer cell growth inhibitory biosynthetic product designated stylostatin 2. The new peptide exhibited a high-resolution molecular ion peak at m/z 768.4647 corresponding to molecular formula $C_{40}H_{61}N_7O_8$. Amino acid analyses indicated the presence of phenylalanine, proline (x2), leucine, isoleucine (x2) and serine. Presence of the amino acids was confirmed by 2D-NMR employing $^1H$-$^1H$-COSY, HMQC, and HMBC experiments. The amino acid sequence was identified as cyclo ($Pro^1$-$Leu^2$-$Ile^3$-$Phe^4$-$Ser^5$-$Pro^6$-$Ile^7$) from the HMBC and NOESY/ROESY experiments. The complete $^1H$- and $^{13}C$-NMR assignments for stylostatin 2 have been summarized in Table 1.

TABLE 1

The High Field (500 MHz) NMR Assignments for Stylostatin 2 (1) in DMSO-$d_6$:

| Position Number | $^1H$(d) | $^{13}C$(d) | HMBC[a] | NOESY/ROESY[b,c] |
|---|---|---|---|---|
| $Pro^1$ | | | | |
| 1 | — | 170.74 | 2-H, 3-H, $Leu^2$ N-H | |
| 2 | 4.0126(t, J=7.1Hz) | 60.684 | 3-H, 4-H, $Leu^2$ N-H | 3-H, 4-H, $Leu^2$ N-H |
| 3 | 1.72, 2.04(m) | 29.338 | 2-H, 5-H | |
| 4 | 1.74, 2.0(m) | 24.685 | 2-H, 3-H, 5-H | |
| 5 | 3.58, 4.38(m) | 48.128 | 3-H, 4-H | |
| $Leu^2$ | | | | |
| 1 | — | 171.72 | 2-H, 3-H, $Lle^7$ N-H | |
| 2 | 3.5(m) | 54.084 | N-H, 3-H | 3-H |
| 3 | 1.537, 2.14(m) | 36.964 | N-H, 4-H, 2-H | |
| 4 | 1.4(m) | 24.637 | 3-H, 5-H, 5'-H | |

TABLE 1-continued

The High Field (500 MHz) NMR Assignments for Stylostatin 2 (1) in DMSO-$d_6$:

| Position Number | $^1H$(d) | $^{13}C$(d) | HMBC$^a$ | NOESY/ROESY$^{b,c}$ |
|---|---|---|---|---|
| 5 | 0.77 | 20.797 | 3-H | |
| 5' | 0.82 | 23.111 | 3-H | |
| NH | 8.64(br s) | — | | 2-H, (4-H), Pro$^1$ 2-H |
| Lle$^3$ | | | | |
| 1 | — | 169.65 | 2-H, Phe$^4$ N-H, Phe$^4$ 2-H | |
| 2 | 4.13(m) | 59.117 | N-H, 3-H | 3-H, 4-H |
| 3 | 1.4(m) | 36.703 | 2-H, 4-H, 3'-H, 5-H | |
| 4 | 1.38, 1.06 | 23.851 | 2-H, 3'-H, 5-H | |
| 5 | 0.62 | 9.457 | 4-H, 3-H | |
| 3' | 0.80 | 14.422 | 2-H, 3-H, 4-H | |
| NH | 7.21 | — | | 2-H, 3-H |
| Phe$^4$ | | | | |
| 1 | — | 170.9 | 2-H, 3-H, N-H, Ser$^5$ N-H | |
| 2 | 4.13(m) | 55.234 | N-H, 3-H | 3-H |
| 3 | 2.815(dd, 9.8 & 12.7Hz), 3.129m) | 36.897 | 2-N, ortho-H | (ortho-H) |
| Phe$^4$ | | | | |
| 4 | — | 136.90 | meta-H | |
| ortho | 7.3 | 129.79 | | |
| meta | 7.26 | 127.93 | | |
| para | 7.2 | 126.32 | | |
| NH | 7.16 | — | | 2-H, (3-H Ser$^5$-OH), Lle$^3$ 4-H, Lle$^7$ 3-H |
| Ser$^5$ | | | | |
| 1 | — | 168.6 | 2-H, 3-H, N-H Pro$^6$ 5-H | |
| 2 | 3.8851(t, 7.05 Hz) | 55.072 | N-H, O-H, 3-H | (OH), 3-H, Lle$^7$ NH, Leu$^2$ 2-H, Pro$^6$ 2-H |
| 3 | 3.43(m) | 60.737 | N-H, 2-H, O-H | (OH,Pro$^6$ 2-H) |
| OH | 5.0804(t, 5.8Hz) | — | | Pro$^6$ 2-H, Pro$^6$ 5-H, Pro$^1$ 2-H |
| | 8.64(br s) | — | | (OH, 2-H), 3-H, Phe$^4$ 2-H, (Leu$^2$ 2-H) |
| Pro$^6$ | | | | |
| 1 | — | 171.02 | 2-H, 3-H Lle$^3$ N-H | |
| 2 | 4.6989(d, 7.6Hz) | 60.499 | 3-H, 4-H | 3-H, (4-H) |
| 3 | 1.9, 2.36 | 30.691 | 2-H, 4-H, 5-H | |
| 4 | 1.9, 1.5 | 22.109 | 2-H, 3-H, 5-H | |
| 5 | 3.50, 3.34 | 46.235 | 2-H, 3-H | |
| Lle$^7$ | | | | |
| 1 | — | 171.2 | 2-H | |
| 2 | 4.1326(dd, 8.6 & 10.7Hz) | 54.962 | 3-H, 3'-H, N-H, | 3-H, Pro$^1$ 5-H |
| 3 | 2.02(m) | 34.728 | 2-H, 4-H, 3'-H, N-H | |
| 4 | 1.134, 1.514 | 24.19 | 4-H, 3-H, 3'-M, 5-H | |
| 5 | 0.82 | 10.053 | 4-H | |
| 3' | 0.846 | 14.824 | 4-H | |
| NH | 9.4135(d, 8.3 Hz) | — | — | 3-H, 2-H, Ser$^5$ 2-H |

$^a$Mixing time = 60 μs;
$^b$Mixing time for NOESY = 200 μs, for ROESY = 50 μs;
$^c$entries in paranthesis refer only to ROESY peaks Subsequently, stylostatin 2 was also isolated ($1.3\times10^{-5}$% yield) from the Western Pacific Ocean sponge Phakellia costata.

Interestingly, the γ-carbon of Pro$^6$ resonated up field at δ 22.10 compared to that of Pro$^1$ at δ 24.68 which suggested the peptide bond between the Ile$^7$ and Pro$^1$ units might be trans and the peptide bond between Ser$^5$ and Pro$^6$ might be cis. Further support for this assumption was provided by differences in the chemical shifts of the β- and γ-carbons (Δδβγ) in the two proline units. Proline cis-trans isomers can be distinguished in solution by the chemical shift differential of the β- and γ-carbons. Pook demonstrated, with a series of cis- and trans-proline models, that the chemical shift differential for these two carbons increases linearly with increasing angle ψ (Pro). In a cis X-Pro, these signals are further separated than in a trans X-Pro. With stylostatin 2 the chemical shifts of the β- and γ-carbons in Pro$^6$ differ by 8.58 ppm. The corresponding signals of Pro$^1$ differ by 4.64 ppm, indicating that the former peptide bond is cis and the latter trans. Strong NOESY/ROESY cross peaks between the $Ser^5$ α-proton and the $Pro^6$ α-proton further supported this observation.

To confirm the proposed structure, a single-crystal X-ray crystallographic analysis of stylostatin 2 was performed. Colorless crystals thereof were produced with difficulty from a methanol solution. The crystals were extremely unstable-losing solvent of crystallization readily at ambient temperatures. Immersion of the crystals in the mother liquor from crystallization in a glass capillary provided sufficiently stable conditions for data collection. Each molecule of stylostatin 2 was found to be associated with a single molecule of methanol. Based upon the A . . . B bond length observed in an A-H . . . B hydrogen bond, stylostatin 2 appears to be involved in both intermolecular and intramolecular H-bonding. Generally, peptide N-H . . . O bonds have an A . . . B length in the range of ~2.79±0.12 Å and O-H . . . O bonds have an A . . . B length in the range of 2.76±0.09 Å. Thus, intramolecular H-bonding seems probable between the N10 . . . 029 (2.841 Å) hetero atoms. From the bond distances, intermolecular H-bonding between N4 . . . 050 ($Ser^5$ amide-$Leu^2$ carbonyl at 2.841 Å), 031 . . . 057 ($Ser^5$ hydroxyl-$CH_3OH$ at 2.733 Å), 032 . . . 057 ($Ser^5$ carbonyl-$CH_3OH$ at 2.725 Å) and N16 . . . 055 ($Leu^2$ amide-$Ile^3$ carbonyl at 2.883 Å) seems predictable.

The absolute configuration of the N-pentafluoropropionyl isopropyl amino acid ester derivatives prepared from the acid hydrolysate of stylostatin 2 was ascertained using chiral gas chromatographic analysis. From these experiments, isoleucine present in the peptide was found to be (S). Thus, from the relative stereochemistry obtained from the X-ray data, all the amino acids present were assigned the S absolute configuration.

In the solid state, stylostatin 2 contains all-trans, undistorted peptide bonds except for a cis bond between $Ser^5$ and $Pro^6$ (suggested by the NMR studies). The pyrrolidine ring of $Pro^6$ has a $C^\gamma$-exo conformation ($\chi^1$=32.0, $\chi^2$=–41.3, $\chi^3$=34.2, $\chi^4$=–13.5) and that of $Pro^1$ a $C^\gamma$-exo conformation ($\chi^1$=–11.7, $\chi^2$=21.9, $\chi^3$=21.3, $\chi^4$=11.1). A type VI (a) β-turn occurs at the $Ser^5$—$Pro^6$ juncture incorporating the cis peptide bond. All values for the pairs φ, ψ fall within the allowed regions for L-amino acid units except for $Leu^2$ which presents the values 69.8°, 0.5°, appreciably higher in energy near the left-handed helical region and is quite unusual.

Because of the initial cancer cell growth inhibitory properties of stylostatin 2 and the unexpected conformational aspects, extended antineoplastic evaluations of this cyclic peptide are planned. Quadruplicate tests of stylostatin 2 against the U.S. National Cancer Institute panel of 60 human cancer cell lines revealed an overall panel-averaged $GI_{50}$ concentration of $6.2\times10^{-6}$M. COMPARE analyses of the TGI-based mean graph of stylostatin (shown below) 2 against the TGI mean graph database of the known "standard agents" revealed the highest correlations with known tubulin-interactive antimitotics (e.g. vinblastine, correl. coeff. >0.7).

National Cancer Institute Developmental Therapeutics Program
Mean Graphs stylostalin -2, natural NSC: V 4684 Units: Molar SSPL: r Exp. ID: Averaged
Report Date: October 27, 1994 HIgh Cone: -4.6

| Panel/Cell Line | $Log_{10}$ GI50 | $Log_{10}$ TGI | $Log_{10}$ LC50 |
|---|---|---|---|
| **Leukemia** | | | |
| CCRF-CEM | -4.85 | -4.60 | -4.60 |
| HL-60(TB) | -5.70 | -4.77 | -4.60 |
| K-562 | -4.96 | -4.60 | -4.60 |
| MOLT-4 | -5.00 | -4.62 | -4.60 |
| RPMI-8226 | -5.00 | -4.62 | -4.60 |
| SR | -5.27 | -4.68 | -4.60 |
| **Non-Small Cell Lung Cancer** | | | |
| A549/ATCC | -5.05 | -4.60 | -4.60 |
| EKVX | -4.92 | -4.62 | -4.60 |
| HOP-62 | -5.28 | -4.80 | -4.60 |
| HOP-92 | -4.80 | -4.60 | -4.60 |
| NCI-H226 | -5.28 | -4.80 | -4.60 |
| NCI-H23 | -5.10 | -4.66 | -4.60 |
| NCI-H322M | -5.18 | -4.77 | -4.66 |
| NCI-H460 | -5.21 | -4.70 | -4.60 |
| NCI-H522 | -6.60 | -4.89 | -4.60 |
| **Colon Cancer** | | | |
| COLO 205 | -5.22 | -4.77 | -4.62 |
| HCC-2998 | -4.92 | -4.72 | -4.60 |
| HCT-116 | -5.34 | -4.74 | -4.60 |
| HCT-15 | -4.82 | -4.60 | -4.60 |
| HT29 | -5.19 | -4.72 | -4.66 |
| KM12 | -5.22 | -4.60 | -4.60 |
| SW-620 | -5.06 | -4.60 | -4.60 |
| **CNS Cancer** | | | |
| SF-268 | -4.92 | -4.60 | -4.60 |
| SF-295 | -5.29 | -4.80 | -4.60 |
| SF-539 | -5.39 | -5.06 | -4.72 |
| SNB-19 | -5.00 | -4.60 | -4.60 |
| SNB-75 | -5.24 | -4.85 | -4.60 |
| U251 | -5.12 | -4.70 | -4.62 |

GI50
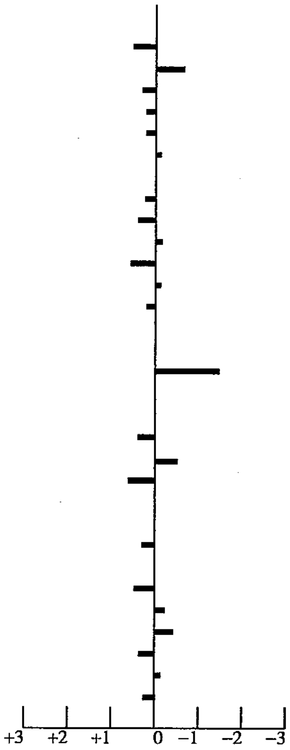

TGI
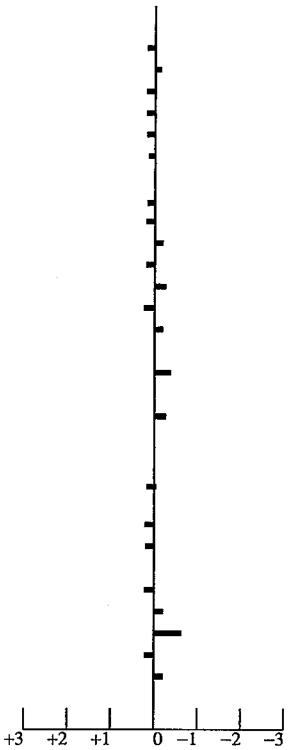

LC50
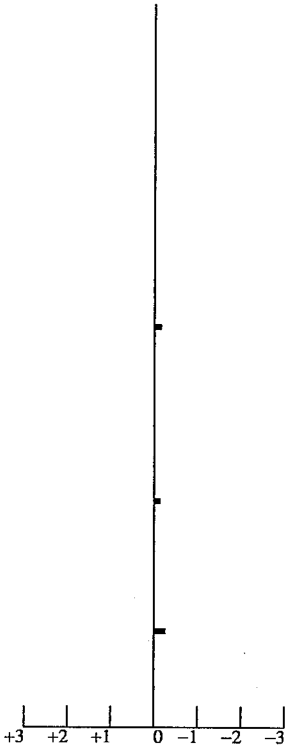

-continued

National Cancer Institute Developmental Therapeutics Program
Mean Graphs stylostalin -2, natural NSC: V 4684 Units: Molar SSPL: r Exp. ID: Averaged
Report Date: October 27, 1994 HIgh Conc: –4.6

| Panel/Cell Line | $Log_{10}$ GI50 | $Log_{10}$ TGI | $Log_{10}$ LC50 |
|---|---|---|---|
| Melmoma | | | |
| LOXIMVI | –5.24 | –4.70 | –4.60 |
| MALME-3M | –5.59 | –4.66 | –4.60 |
| M14 | –5.28 | –4.68 | –4.60 |
| SK-MEL-2 | –5.15 | –4.85 | –4.60 |
| SK-MEL-28 | –5.18 | –4.60 | –4.60 |
| SK-MEL-5 | –6.02 | –4.96 | –4.62 |
| UACC-257 | –5.08 | –4.70 | –4.60 |
| UACC-62 | –5.46 | –4.96 | –4.85 |
| Ovarian Cancer | | | |
| IGROV1 | –4.96 | –4.60 | –4.60 |
| OVCAR-3 | –5.77 | –5.17 | –4.72 |
| OVCAR-4 | –4.70 | –4.60 | –4.60 |
| OVCAR-5 | –5.01 | –4.60 | –4.60 |
| OVCAR-8 | –4.96 | –4.60 | –4.60 |
| SK-OV-3 | –5.28 | –4.74 | –4.60 |
| Renal Cancer | | | |
| 786-0 | –5.36 | –4.77 | –4.60 |
| A498 | –4.28 | –4.80 | –4.60 |
| ACHN | –4.96 | –4.60 | –4.60 |
| CAKI-1 | –5.00 | –4.60 | –4.60 |
| RXF-393 | –5.30 | –4.92 | –4.60 |
| SN12C | –4.89 | –4.60 | –4.60 |
| TK-10 | –4.72 | –4.60 | –4.60 |
| U0-31 | –5.03 | –4.72 | –4.62 |
| Prostate Cancer | | | |
| PC-3 | –5.26 | –4.60 | –4.60 |
| DU-145 | –5.08 | –4.68 | –4.60 |
| Breast Cancer | | | |
| MCF7 | –5.52 | –4.92 | –4.62 |
| MCF7/ADR-RES | –4.60 | –4.60 | –4.60 |
| MDA-MB-231/ATCC | –5.02 | –4.62 | –4.60 |
| HS578T | –5.32 | –4.77 | –4.60 |
| MDA-MB-435 | –5.96 | –5.05 | –4.72 |
| MDA-N | –6.00 | –4.96 | –4.60 |
| BT-549 | –5.36 | –4.68 | –4.60 |
| T-47D | –5.04 | –4.60 | –4.60 |
| MG_MID | –5.21 | –4.72 | –4.62 |
| Delta | 1.40 | 0.45 | 0.24 |
| Range | 2.00 | 0.57 | 0.25 |

GI50

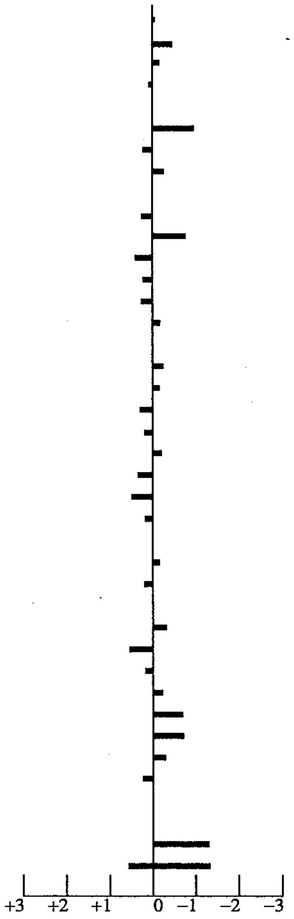

TGI

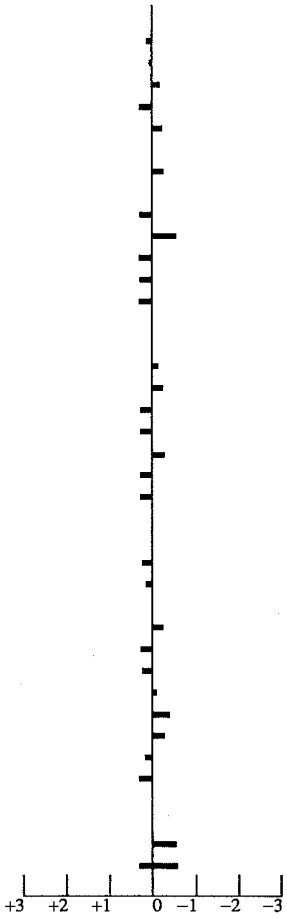

LC50

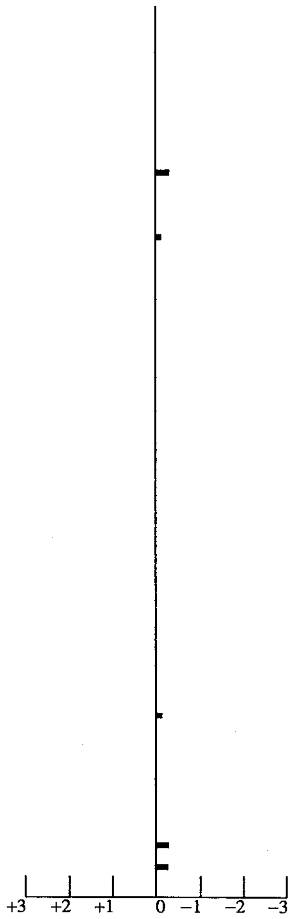

All solvents employed for chromatographic separations were redistilled. The SEPHADEX LH-20 (25–100 μm) used for gel permeation and partition chromatography was supplied by Pharmacia Fine Chemicals AB, Uppsala, Sweden. SILICA GEL GF UNIPLATES for TLC were obtained from Analtech Inc., Newark, DE. The TLC plates were viewed with UV light and/or developed with a ceric sulfate-sulfuric acid spray (heating to approximately 150° C. for 5–10 minutes). Gas chromatographic analyses were conducted with a Chirasil-Val III FSOT capillary column (50 m×0.25 mm). Amino acid analyses were performed with a HEWLETT-PACKARD reversed-phase HPLC column ODS HYPERSIL C18 (2.1×200 mm). NMR data were recorded using deuterodimethyl sulphoxide as solvent with BRUKER AM 400 (ASPECT 3000) and VARIAN UNITY 500 spectrometers. The X-ray crystallography experiments were conducted using an Enraf-Nonius CAD-4 diffractometer.

The isolation of Stylostatin 2 was accomplished by two methods. First, it was isolated from Stylotella sp. A 500 kg (wet wt) recollection (1986) of the Papua New Guinea marine sponge Stylotella sp. (Class Desmospongiae, Order Hadromerida) was extracted and fractioned (PS bioassay) as previously reported and identified above. Partition chromatography of fraction B on a SEPHADEX LH-20 column (225×4.5 cm) with 3:1:1 hexane-toluene-methanol as eluent provided active fraction C (0.14 g). Final purification of fraction C was achieved by fractional crystallization from aqueous methanol. Stylostatin 2 was isolated as a colorless crystalline solid (0.1 g, $2\times10^{-5}$% yield); mp 228–229° C. (capillary tube uncorrected); $[\alpha]_D^{25}$–128° (c 0.2, $CH_3OH$); HRFAB m/z 768.4647, Calcd. 768.4640 for $C_{40}H_{61}N_7O_8$; IR (KBr): 3325, 3295, 2965, 2936, 2876, 1653, 1616, 1532, 1449, 1385, 1331, 1242, 1067, 748 and 702 $cm^{-1}$; and refer to Table 1 above for the $^1H$- and $^{13}C$-NMR data.

Secondly, stylostatin 2 was also isolated from Phakellia costata. A P388 cell line active methylene chloride soluble fraction prepared from 500 Kg (wet wt) of Phakellia costata collected (1987) in the Federated States of Micronesia (Chuuck) was chromatographed using a series of gel permeation and partition SEPAHADEX LH-20 columns employing methanol, methylene chloride-methanol (3:2), hexane-toluene-methanol (3:1:1) and hexane-methylene chloride-methanol (8:1:1→3:1:1) eluent techniques to yield a more concentrated active fraction. Final separation was accomplished by HPLC (on SILICA GEL-60 with hexane-methylene chloride-methanol 10:5:1, as mobile phase) to furnish stylostatin 2 (63.5 mg, $1.3\times10^{-5}$ yield).

Stylostatin 2 chiral assignments were accomplished in the following manner. The peptide (1 mg) was hydrolyzed with 12N propionic acid-hydrochloric acid (1:1) at 160° C. for 15 minutes. The derived amino acids were converted to N-pentafluoropropionyl isopropyl ester derivatives, and the configuration of isoleucine (retention time 18.17 m, versus standard L-Ile 18.17 and D-Ile 17.17 m) was determined by chiral capillary chromatography.

Stylostatin 2 X-ray Crystal Structure were determined as follows. Stylostatin 2 grown with difficulty from methanol solution, were quite unstable, and readily lost solvent of crystallization at ambient temperatures. Consequently a crystal (0.30×0.30×0.40 mm) of stylostatin 2 crystallized from methanol was mounted inside a glass capillary tube with the crystal immersed in mother liquor. Data collection was performed at 26±1° C. Crystal data: $C_{40}H_{61}N_7O_8.CH_3OH$, monoclinic space group $P2_1$, with a =13.660 Å, b=10.059 Å, c=16.713 Å, β=95.054°, V=2287.54 $Å^3$, λ(Cu Kα)=1.54184 Å, $\rho_o$=1.172 g $cm^{-3}$, $\rho_c$=1.162 g $cm^{-3}$ for Z=2 and F. W. =800.01, F(000)=864. All reflections corresponding to a complete quadrant, with 2θ≦140° were measured using the ω/2θ scan technique. After Lorentz and polarization corrections, merging of equivalent reflections and rejection of systematic absences, 3595 unique reflections remained, of which 2251 were considered observed ($I_o>3\sigma(I_o)$) and were used in the subsequent structure determination and refinement. Linear and anisotropic decay corrections were applied to the intensity data as well as an empirical absorption correction (based on a series of psi-scans). Near the conclusion of the refinement process, an additional least-squares absorption correction was also made in the data using the CRYSTALS program DIFABS. Concerted efforts directed at solving the structure using the direct-methods programs MULTAN and SHELXS-86 failed. Similarly, the vector search program PATSEE also failed. In each case, the absence of any recognizable fragments precluded further structure expansion. Structure determination was eventually accomplished with the direct-methods program SIR88.

All non-hydrogen atoms, with the exception of one aromatic ring atom of the phenylalanine residue and one terminal methyl atom of an isoleucine moiety, were located on the first run of SIR88, using the default settings. Subsequent difference Fourier maps revealed the remaining atoms as well as the presence of an additional molecule of methanol associated with each molecule of stylostatin 2. The remaining H atom coordinates were calculated at optimum positions for the cyclic peptide and added in the final stages of least-squares refinement and structure-factor calculation process, but were not refined. The atoms of the cyclic peptide structure, in addition to the 2 solvate atoms of methanol, were refined in a full-matrix least-squares process with CRYSTALS, using the $1/\delta_F^2$ weighting scheme. Anomalous dispersion effects were included in $F_c$. The final cycle of refinement included 505 variable least-squares parameters (anisotropic refinement on all but two of the peptide non-hydrogen atoms). Atoms C34 and C43 (present in the two proline rings) were refined isotropically due to the tendency of their thermal parameters to refine to "non-positive definite" values when refined anisotropically. The final model for stylostatin 2 converged to unweighted and weighted standard crystallographic residuals of R=0.136 and Rw=0.129. Final bond distances and angles were all within acceptable limits.

The final structure of stylostatin 2 was determined to have the heptapeptide sequence cyclo (Pro-Leu-Ile-Phe-Ser-Pro-Ile). The absolute stereochemical assignment of stylostatin 2 was based upon the known absolute stereochemistry of isoleucine. Thus, the absolute configuration at the nine chiral centers of stylostatin 2, using the numbering shown in FIG. 2 follows: 2S, 5S, 8S, 11S, 14S, 17S, 20S, 37S, 51S. A final difference Fourier map showed minimal residual electron density in regions not associated with the main peptide molecule or methanol. The highest peak in the final difference Fourier had a height of 0.47 e/$Å^3$. Stylostatin 2 appears to be involved in both intermolecular and intramolecular H-bonding, based upon the total A . . . B bond length observed in an A-H . . . B hydrogen bond.

The administration of stylostatin 2, its synthetic counterparts, and its pharmaceutically active, physiologically compatible derivatives is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like neoplasms.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg. As used herein, mg/kg means weight of active ingredient in milligrams divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE I

Several dosage forms are available embodying the present invention. They are shown in the following examples in which the notation "active ingredient" signifies stylostatin 2, its synthetic counterpart and the non-toxic pharmaceutically active derivatives thereof.

COMPOSITION "A"

Hard-Gelatin Capsules

One thousand two-piece hard gelatin capsules for oral use, each capsule containing 20 mg of an active ingredient are prepared from the following types and amounts of ingredients:

| | |
|---|---|
| Active ingredient, micronized | 20 gm |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 mg amounts by substituting 5 gm, 25 gm and 50 gm of an active ingredient for the 20 gm used above.

COMPOSITION "B"

Soft Gelatin Capsules

One-piece soft gelatin capsules for oral use, each containing 20 mg of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient are prepared from the following types and amounts of ingredients.

| | |
|---|---|
| Active ingredient, micronized | 20 gm |
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 gm and 10 gm of an active ingredient for the 20 gm used above.

COMPOSITION "D"

Oral Suspension

One thousand ml of an aqueous suspension for oral use, containing in each teaspoonful (5 ml) dose, 5 mg of an active ingredient, is prepared from the following types and amounts of ingredients:

| | |
|---|---|
| Active ingredient, micronized | 1 gm |
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml, 30 mg of an active ingredient for treating a neoplastic disease, is prepared from the following types and amounts of ingredients:

| | |
|---|---|
| Active ingredient, micronized | 30 gm |
| Polysorbate 80 | 5 gm |
| Methylparaben | 2.5 gm |
| Propylparaben | 0.17 gm |
| Water for injection, q.s. 1000 ml | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 ; gm and containing 20 mg of an active ingredient are prepared from the following types and amounts of ingredients:

| | |
|---|---|
| Active ingredient, micronized | 1.5 gm |
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation is prepared, containing 20 mg of an active ingredient per ml of suspension, from the following types and amounts of ingredients:

| | |
|---|---|
| Active ingredient, micronized | 1.5 gm |
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten grams of an active ingredient in bulk form is finely divided by means of an air micronizer. The micronized powder is divided into individual doses of 20 mg and packaged.

The foregoing powders are useful for treating a neoplastic disease by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease by the inhalation of 300 mg one to four times per day.

COMPOSITION "K"

Hard-Gelatin Capsules

One hundred two-piece hard-gelatin capsules were prepared for oral use, each capsule containing 200 mg of an active ingredient. The active ingredient is finely divided by means of an air micronizer and encapsulated in the usual manner. The foregoing capsules are useful for treating a neoplastic disease, by the oral administration of one or two capsules, one to four times a day.

Using the procedure above, capsules are similarly prepared containing an active ingredient in 50, 250 and 500 gm of the active ingredient for the 200 gm used above.

From the foregoing, it is readily apparent that a useful embodiment of the present invention has been herein described and illustrated which fulfills all of the aforestated objectives in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

We claim:

1. A substantially pure composition of matter denominated stylostatin 2 and having the structure:

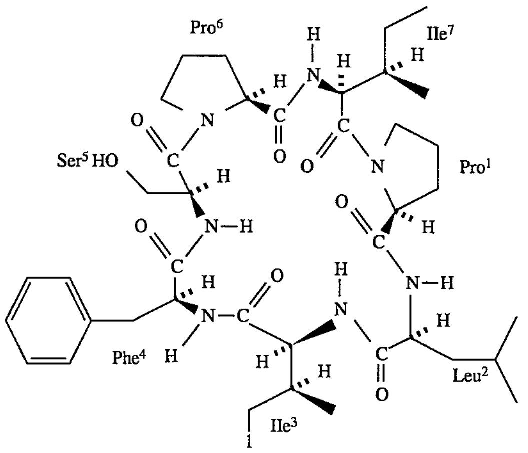

;

2. A composition of matter comprising a pharmaceutically acceptable carrier and, as its essential active ingredient, a small but effective amount of stylostatin 2.

* * * * *